US00PP08341P

United States Patent [19]

Meilland

[11] Patent Number: Plant 8,341

[45] Date of Patent: Aug. 10, 1993

[54] ROSE PLANT — MEITORPO VARIETY

[75] Inventor: Alain A. Meilland, Antibes, France

[73] Assignee: The Conard-Pyle Company, West Grove, Pa.

[21] Appl. No.: 848,163

[22] Filed: Mar. 10, 1992

[30] Foreign Application Priority Data

Aug. 28, 1991 [NL] Netherlands ..... R00 1782

[51] Int. Cl.[5] ..... H01H 5/00

[52] U.S. Cl. ..... Plt./20

[58] Field of Search ..... Plt./20, 21

*Primary Examiner*—Howard J. Locker

*Attorney, Agent, or Firm*—Burns, Doane, Swecker & Mathis

[57] ABSTRACT

A new and distinct variety of Hybrid Tea rose plant is provided which abundantly forms attractive small double blossoms which are red in coloration. The blossom coloration is Vermilion Red on the upper surface and Cherry Red on the under surface. The blossoms exhibit an excellent life when cut and placed in a vase. The plant exhibits an upright growth habit, forms very vigorous vegetation, and is well suited for cut flower production. An excellent forcing capacity is exhibited when grown under greenhouse conditions.

1 Drawing Sheet

SUMMARY OF THE INVENTION

The new variety of Hybrid Tea rose plant was created by artificial pollination wherein two parents were crossed which previously had been studied in the hope that they would contribute the desired characteristics. The female parent (i.e., the seed parent) of the new variety was the Jacqueline variety (U.S. Plant Pat. No. 2,183). The male parent (i.e., the pollen parent) was the product of the cross of the Meinobroc variety (U.S. Plant Pat. No. 6,171) and the Jelvanica variety (nonpatented in the United States). The parentage of the new variety can be summarized as follows:

Jacqueline × (Meinobroc × Jelvanica).

The seeds resulting from the above pollination were sown and 36 small plants were obtained which were physically and biologically different from each other. Selective study resulted in the identification of a single plant of the new variety.

It was found that the new variety of Hybrid Tea rose plant of the present invention possesses the following combination of characteristics:

(a) forms in abundance attractive double blossoms which are Vermilion Red on the upper surface and Cherry Red on the under surface,
(b) forms blossoms which exhibit an excellent life when cut and placed in a vase,
(c) exhibits very vigorous vegetation,
(d) exhibits an upright growth habit,
(e) is particularly suited for cut flower production and exhibits an excellent capacity to be forced under greenhouse conditions, and
(f) is not particularly affected by cryptogamic diseases.

The blossoms are particularly attractive at the bud stage and during the course of opening.

The new variety well meets the needs of the horticultural industry and is well suited for use in the production of cut flowers under greenhouse conditions.

The new variety has been found to undergo asexual propagation in France and in the United States by a number of routes, including budding, grafting, cuttage, etc. Asexual propagation by the above mentioned methods as performed in France has shown that the characteristics of the new variety are strictly transmissible from one generation to another.

The new vareity has been named the Meitorpo variety.

BRIEF DESCRIPTION OF THE PHOTOGRAPH

The accompanying photograph shows as nearly true as it is reasonably possible to make the same, in a color illustration of this character, typical specimens of the plant parts of the new variety. The rose plants of the new variety were two years of age and were observed during August while budded on *Rosa indica* understock and growing in greenhouses at Cap d'Antibes, France.

DETAILED DESCRIPTION

Figures 1, 2, 3, 4, 5, 6, 7, 8, 9, 10, 11, 12, 13, 14, 15, 16:
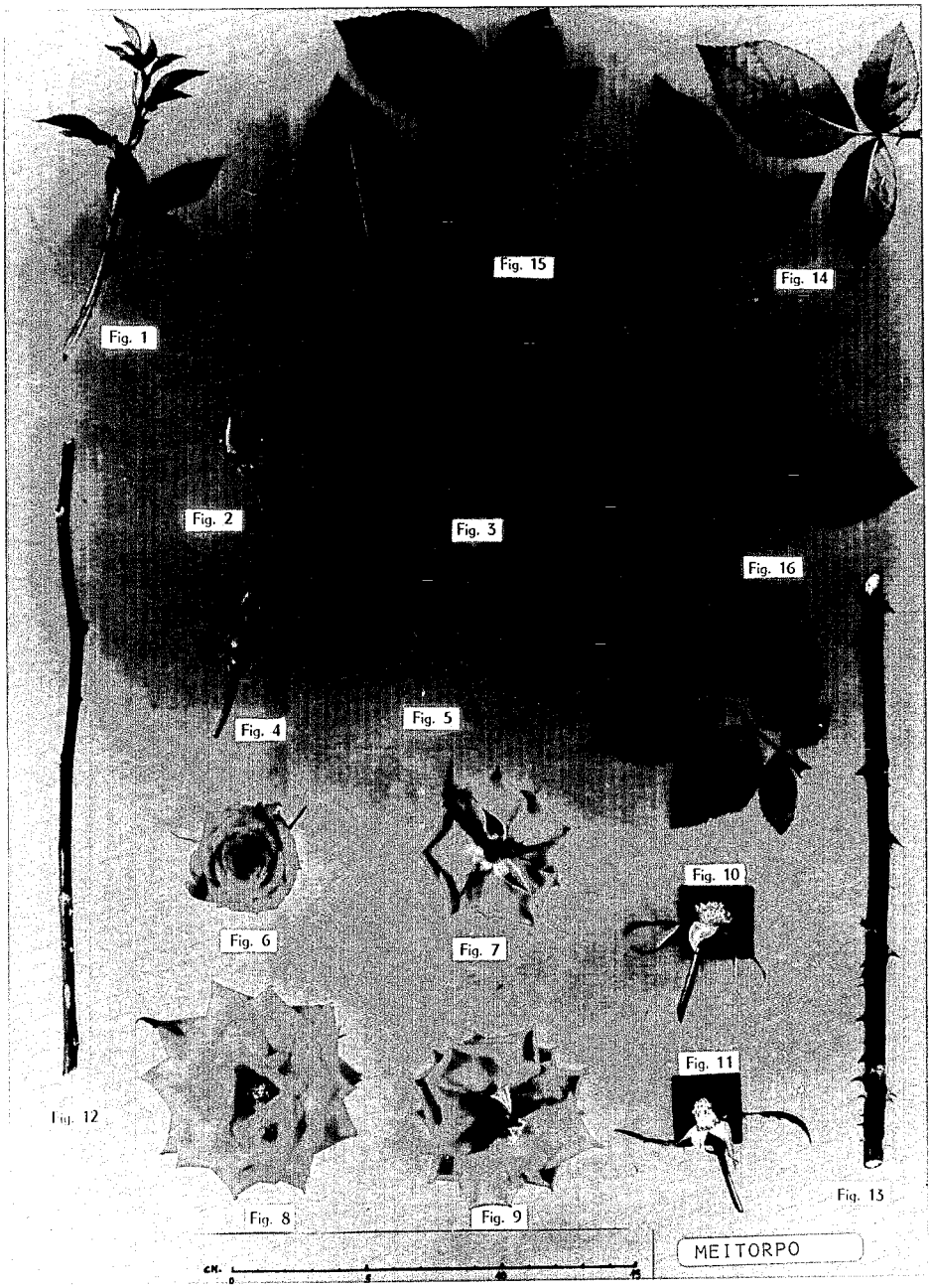
FIG. 1 illustrates a specimen of a young shoot.
FIG. 2 illustrates a specimen of a floral bud before the opening of the sepals.
FIG. 3 illustrates a specimen of a floral bud at the opening of the sepals.
FIG. 4 illustrates a specimen of a floral bud at the opening of the petals.
FIG. 5 illustrates a specimen of a flower in the course of opening.
FIG. 6 illustrates a specimen of an open flower — plan view — obverse.
FIG. 7 illustrates a specimen of an open flower — plan view — reverse.
FIG. 8 illustrates a specimen of a fully open flower — plan view — obverse.
FIG. 9 illustrates a specimen of a fully open flower — plan view — reverse.
FIG. 10 illustrates a specimen of a floral receptacle showing the arrangement of the stamens and pistils.
FIG. 11 illustrates a specimen of a floral receptacle showing the arrangement of the pistils (stamens removed)
FIG. 12 illustrates a specimen of a flowering stem.
FIG. 13 illustrates a specimen of a main branch.
FIG. 14 illustrates specimens of leaves with three leaflets — plan view — upper surface (lower left) and lower surface (upper right)
FIG. 15 illustrates specimens of leaves with five leaflets — plan view — upper surface (upper right) and lower surface (lower left)
FIG. 16 illustrates specimens of leaves with seven leaflets — plan view — upper surface (top) and lower surface (bottom).

The chart used in the identification of the colors is that of The Royal Horticultural Society (R.H.S. Colour Chart). The description is based on the observation of two year old plants made during August while budded on *Rosa indica* understock and growing in greenhouses at Cap d'Antibes, France. The coloration in common terms precedes reference to the chart.

Class: Hybrid Tea.

Plant:

*Height.*—When plants are cut to a height of 85 cm., flowering stems are produced having a length of approximately 30 to 60 cm. When grown outdoors at Wasco, Calif., the plants commonly reach a height of approximataely 80 to 90 cm. at the end of one growing season.

*Habit.*—Upright.

Branches:

*Color.*—Young stems: medium green, Green Group 143A. Adult wood: medium green, Green Group 143B.

*Thorns.*—Size: small. Quantity: average. Color: greenish on young stems and greenish-pink changing to tan on mature wood.

Leaves:

*Stipules.*—Adnate, pectinate, wide and linear.

*Petioles.*—Upper surface: striped reddish green on young foliage and medium green on adult foliage with very glandular edges. Under surface: light green, and bears numerous prickles.

*Leaflets.*—Number: 3, 5 (most often), and 7. Shape: elliptic. Serration: single and regular. Texture: consistent. General appearance: dense, semi-dull foliage. Color (young foliage): Upper surface: medium green, Green Group 143A, more or less suffused with reddish brown. Under surface: medium green, Green Group 143B, more or less suffused with reddish brown. Color (adult foliage): Upper surface: dark green, Green Group 137A. Under surface: greyish green, Greyed-Green Group 191A.

Inflorescence:

*Number of flowers.*—Usually one single bloom per stem.

*Peduncle.*—Smooth, and light green. The length is approximately 5 to 7 cm. on average.

*Sepals.*—Upper surface: tomentose, greenish in coloration. Under surface: Medium green and the outer sepals are more or less appendiculated.

*Buds.*—Shape: oblong. Length: approximately 2 to 2.5 cm. on average. Size: small. Color upon opening: Upper surface: dark Vermilion Red, Red Group 44A. Under surface: Strawberry Red, Red Group 46B.

*Flower.*—Shape: cup-like with substantially flat top and fully double. Diameter: approximately 7.5 to 8 cm. on average. Color (when opening begins): Upper surface: dark Vermilion Red, Red Group 44A. Under surface: Strawberry Red, Red Group 46B. Color (when blooming): Upper surface: dark Vermilion Red, Red Group 44A. Under surface: Strawberry Red, Red Group 46B. Color (at end of opening): Upper surface: Cherry Red, Red Group 45C, and widely suffused with medium Vermilion Red, Red Group 44B. Under surface: Cherry Red, Red Group 45C, and widely suffused with light Cardinal Red, Red Group 53C. Fragrance: none. Lasting quality: long lasting when cut and placed in a vase. Petal number: approximately 25 to 32 on average. Petal shape: rounded to oval. Texture: consistent. Petal drop: good. Stamen number: approximately 67 on average. Anthers: Ochre, and tinged with fuschia coloration. Filaments: irregular in height, and dark fuschia in coloration. Pistils: approximately 135 on average. Stigmas: straw colored. Styles: irregular in height, more or less twisted, and fuschia in coloration. Receptacle: light green, smooth, and in longitudinal section at the dehiscence of the anthers it is in the shape of a pitcher.

Development:

*Vegetation.*—Very vigorous.

*Blooming.*—Very abundant.

*Resistance to diseases.*—Excellent.

*Aptitude to be forced.*—Excellent.

I claim:

1. A new and distinct variety of Hybrid Tea rose plant characterized by the following combination of characteristics:

(a) forms in abundance attractive double blossoms which are Vermilion Red on the upper surface and Cherry Red on the under surface,
(b) forms blossoms which exhibit an excellent life when cut and placed in a vase,
(c) exhibits very vigorous vegetation,
(d) exhibits an upright growth habit,
(e) is particularly suited for cut flower production and exhibits an excellent capacity to be forced under greenhouse conditions, and
(f) is not particularly affected by cryptogamic diseases;

substantially as herein shown and described.

* * * * *

MEITORPO
CM.
0
5
10
15